US00PP21945P2

(12) United States Plant Patent
Fell, Jr.

(10) Patent No.: US PP21,945 P2
(45) Date of Patent: May 31, 2011

(54) ***KALANCHOE* PLANT NAMED 'FANTASTIC'**

(50) Latin Name: *Kalanchoe thyrsiflora*
Varietal Denomination: Fantastic

(76) Inventor: David N. Fell, Jr., Hilo, HI (US)

( * ) Notice: Subject to any disclaimer, the term of this patent is extended or adjusted under 35 U.S.C. 154(b) by 0 days.

(21) Appl. No.: 12/660,964

(22) Filed: Mar. 8, 2010

(51) Int. Cl.
*A01H 5/00* (2006.01)

(52) U.S. Cl. ..... Plt./335

(58) Field of Classification Search ..... Plt./335
See application file for complete search history.

*Primary Examiner* — Annette H Para
(74) *Attorney, Agent, or Firm* — C. A. Whealy

(57) ABSTRACT

A new and distinct cultivar of *Kalanchoe* plant named 'Fantastic', characterized by its upright and compact plant habit; vigorous growth habit; greyed purple, greyed green and pale yellow-variegated leaves with undulate margins; and excellent postproduction longevity.

1 Drawing Sheet

Botanical designation: *Kalanchoe thyrsiflora.*
Cultivar denomination: 'Fantastic'.

BACKGROUND OF THE INVENTION

The present invention relates to a new and distinct cultivar of *Kalanchoe* plant, botanically known as *Kalanchoe thyrsiflora*, and hereinafter referred to by the name 'Fantastic'.

The new *Kalanchoe* plant is a naturally-occurring branch mutation of an unnamed selection of *Kalanchoe thyrsiflora*, not patented. The new *Kalanchoe* plant was discovered by the Inventor on a single plant within a population of plants of the parent selection on Jul. 27, 2007 in a controlled greenhouse environment in Aalsmeer, The Netherlands.

Asexual reproduction of the new *Kalanchoe* plant by vegetative terminal cuttings in a controlled environment in Waimanalo, Hi. since Aug. 15, 2007, has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fantastic'. These characteristics in combination distinguish 'Fantastic' as a new and distinct cultivar of *Kalanchoe:*

1. Upright and compact plant habit.
2. Vigorous growth habit.
3. Greyed purple, greyed green and pale yellow-variegated leaves with undulate margins.
4. Excellent postproduction longevity.

Plants of the new *Kalanchoe* can be compared to plants of the parent selection. Plants of the new *Kalanchoe* differ from plants of the parent selection in the following characteristics:

1. Plants of the new *Kalanchoe* and the parent selection differ in leaf coloration as plants of the parent selection have little to no variegation.

2. Leaves of plants of the new *Kalanchoe* are undulating whereas leaves of plants of the parent selection are flat.

Plants of the new *Kalanchoe* can be compared to plants of *Kalanchoe thyrsiflora* 'Bronze Sculpture', not patented. Plants of the new *Kalanchoe* differ from plants of 'Bronze Sculpture' in the following characteristics:

1. Plants of the new *Kalanchoe* and 'Bronze Sculpture' differ in leaf coloration as plants of 'Bronze Sculpture' have red purple and pale green bi-colored leaves.
2. Leaves of plants of the new *Kalanchoe* are undulating whereas leaves of plants of 'Bronze Sculpture' are flat.

BRIEF DESCRIPTION OF THE PHOTOGRAPHS

The accompanying colored photographs illustrate the overall appearance of the new *Kalanchoe* plant, showing the colors as true as it is reasonably possible to obtain in colored reproductions of this type. Colors in the photographs may differ slightly from the color values cited in the detailed botanical description which accurately describe the colors of the new *Kalanchoe* plant.

The photograph at the bottom of the sheet comprises a top perspective view of a typical plant of 'Fantastic' grown in a container.

The photograph at the top of the sheet comprises a close-up view of a typical plant of 'Fantastic'.

DETAILED BOTANICAL DESCRIPTION

The aforementioned photographs and following observations, measurements and values describe plants grown in 12.5-cm containers in Waimanalo, Hi. in an outdoor nursery during the winter and under conditions which closely approximate commercial *Kalanchoe thyrsiflora* production. During the production of the plants, day temperatures ranged from 27° C. to 32° C., night temperatures ranged from 13° C. to 27° C. and light levels ranged from 14,000 to 18,000 foot-candles. Plants were six months old when the photographs and description were taken. In the following detailed description, color references are made to The Royal Horticultural Society Colour Chart, 2007 Edition, except where general terms of ordinary dictionary significance are used.

Botanical classification: *Kalanchoe thyrsiflora* 'Fantastic'.

Parentage: Naturally-occurring branch mutation of an unnamed selection of *Kalanchoe thyrsiflora*, not patented.

Propagation:

*Type.*—By vegetative terminal cuttings.

*Time to initiate roots, summer.*—About 18 days at temperatures of 28° C. to 29° C.

*Time to initiate roots, winter.*—About 21 days at temperatures of 23° C. to 27° C.

*Time to produce a rooted young plant, summer.*—About 45 days at temperatures of 28° C. to 29° C.

*Time to produce a rooted young plant, winter.*—About 50 days at temperatures of 23° C. to 27° C.

*Root description.*—Fine, fleshy; white in color.

*Rooting habit.*—Freely branching; moderately dense.

Plant description:

*Plant and growth habit.*—Upright and compact plant habit; vigorous growth habit; broad undulate leaves arranged in a basal rosette.

*Plant height.*—About 14 cm to 16 cm.

*Plant diameter.*—About 26 cm.

Stem description:

*Internode length.*—About 7 mm.

*Aspect.*—Erect.

*Strength.*—Strong.

*Texture.*—Smooth, glaucous.

*Color.*—Close to 191D.

Foliage description:

*Arrangement.*—Alternate to whorled, simple.

*Length.*—About 10 cm to 12 cm.

*Width.*—About 9 cm to 11 cm.

*Shape.*—Rotund to elliptical.

*Apex.*—Obovate to orbicular.

*Base.*—Attenuate.

*Margin.*—Entire, undulate.

*Texture, upper and lower surfaces.*—Smooth, waxy; leathery; succulent.

*Venation pattern.*—Pinnate; arcuate and reticulate.

*Color.*—Developing leaves, upper surface: Close to 190B to 190C; towards the apex, random sectors close to 4D. Developing leaves, lower surface: Close to 190A to 190B. Fully expanded leaves, upper surface: Close to 191B to 191C, towards the apex, random sectors close to 4D; towards the margins, random sectors of 4D overlain with close to 185A or 185B and random sectors 191B to 191C overlain with close to 183A to 183B or 183C to 183D; venation, close to 191B to 191C. Fully expanded leaves, lower surface: Close to 148B tinted with close to 183D; towards the margins, close to 183B; venation, close to 191B to 191C.

*Petioles, oldest leaves.*—Length: About 2 cm. Diameter: About 3.2 cm. Texture, upper and lower surfaces: Smooth, glaucous. Color, upper surface: Close to 191B to 191C. Color, lower surface: Close to 191C to 191D.

Flower description: Flower development has not been observed on plants of the new *Kalanchoe.*

Temperature tolerance: Plants of the new *Kalanchoe* have been observed to tolerate temperatures from about 2° C. to about 40° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Fantastic' as illustrated and described.

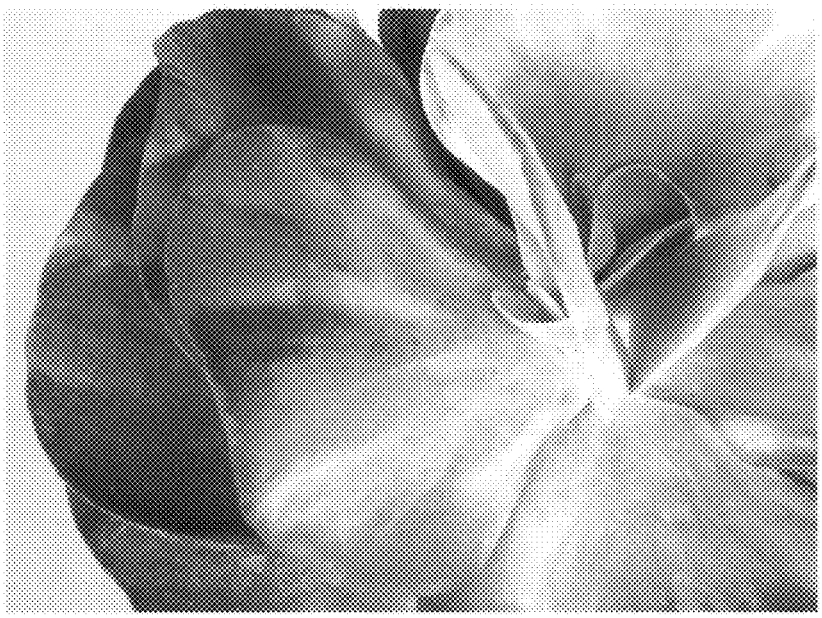
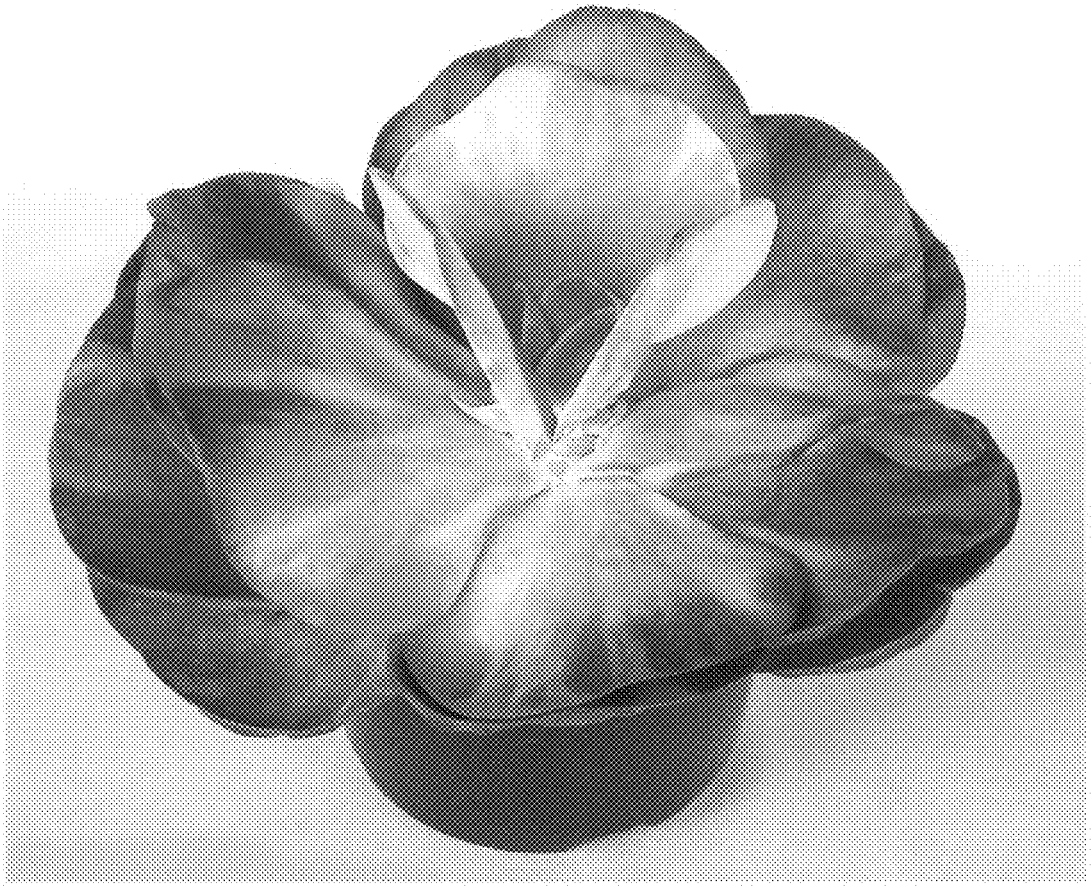

* * * * *